(12) United States Patent
Pottier et al.

(10) Patent No.: US 10,265,406 B2
(45) Date of Patent: Apr. 23, 2019

(54) PHARMACEUTICAL COMPOSITION COMPRISING NANOPARTICLES, PREPARATION AND USES THEREOF

(71) Applicant: NANOBIOTIX, Paris (FR)

(72) Inventors: Agnes Pottier, Paris (FR); Laurent Levy, Paris (FR); Matthieu Germain, Champigny sur Marne (FR)

(73) Assignee: NANOBIOTIX, Paris (FR)

( * ) Notice: Subject to any disclaimer, the term of this patent is extended or adjusted under 35 U.S.C. 154(b) by 0 days.

(21) Appl. No.: 15/105,046

(22) PCT Filed: Dec. 19, 2014

(86) PCT No.: PCT/EP2014/078619
§ 371 (c)(1),
(2) Date: Jun. 16, 2016

(87) PCT Pub. No.: WO2015/091888
PCT Pub. Date: Jun. 25, 2015

(65) Prior Publication Data
US 2016/0310614 A1    Oct. 27, 2016

(30) Foreign Application Priority Data

Dec. 20, 2013 (EP) .................................. 13306799

(51) Int. Cl.
| | | |
|---|---|---|
| *A61K 47/48* | (2006.01) | |
| *A61K 9/00* | (2006.01) | |
| *A61K 33/24* | (2006.01) | |
| *A61K 41/00* | (2006.01) | |
| *A61K 47/60* | (2017.01) | |
| *A61K 47/69* | (2017.01) | |
| *A61N 5/10* | (2006.01) | |

(52) U.S. Cl.
CPC ...... *A61K 47/48861* (2013.01); *A61K 9/0019* (2013.01); *A61K 33/24* (2013.01); *A61K 41/0038* (2013.01); *A61K 47/60* (2017.08); *A61K 47/6923* (2017.08); *A61N 2005/1098* (2013.01)

(58) Field of Classification Search
CPC .......... A61K 41/0038; A61K 47/48861; A61K 9/0019; A61K 47/6923; A61K 47/60; A61K 33/24
See application file for complete search history.

(56) References Cited

U.S. PATENT DOCUMENTS

| | | | |
|---|---|---|---|
| 6,955,639 B2* | 10/2005 | Hainfeld | A61K 41/0038 600/1 |
| 8,845,507 B2 | 9/2014 | Levy et al. | |
| 2009/0130050 A1* | 5/2009 | Kanehira | A61K 9/0009 424/78.17 |
| 2010/0112040 A1 | 5/2010 | Basheer | |
| 2011/0027375 A1 | 2/2011 | Tillement et al. | |
| 2011/0052609 A1 | 3/2011 | Waldoefner et al. | |
| 2011/0213192 A1* | 9/2011 | Levy | A61K 41/0038 600/1 |
| 2013/0177523 A1 | 7/2013 | Ghandehari et al. | |

FOREIGN PATENT DOCUMENTS

| | | |
|---|---|---|
| EP | 2 000 150 | 12/2008 |
| EP | 2 537 530 | 12/2012 |
| FR | 2 922 106 | 4/2009 |
| JP | 2011 509233 | 3/2011 |
| JP | 2013 534459 | 9/2013 |
| WO | WO 2009/147214 | 12/2009 |
| WO | WO 2011/070324 | 6/2011 |
| WO | WO 2011/133228 | 10/2011 |

OTHER PUBLICATIONS deKrafft, K.E. et al. "Zr- and Hf-based nanoscale metal-organic frameworks as contrast agents for computed tomography" *Journal of Materials Chemistry*, Sep. 21, 2012, pp. 18139-18144, vol. 22, No. 35.
Maggiorella, L. et al. "Nanoscale radiotherapy with hafnium oxide nanoparticles" *Future Oncology*, Sep. 1, 2012, pp. 1167-1181, vol. 8, No. 9.
Written Opinion in International Application No. PCT/EP2014/078619, dated Mar. 26, 2015, pp. 1-6.

* cited by examiner

*Primary Examiner* — Mina Haghighatian
(74) *Attorney, Agent, or Firm* — Saliwanchik, Lloyd & Eisenschenk (57) ABSTRACT

The present application relates to a pharmaceutical composition comprising biocompatible nanoparticles or nanoparticles aggregates which allows the appropriate delivery of said biocompatible nanoparticles or nanoparticles aggregates to a target site in a subject in need thereof. The composition indeed allows an accumulation of the biocompatible nanoparticles or nanoparticles aggregates it comprises into the targeted tissue of the subject of at least 4 milligram (mg) nanoparticles or nanoparticles aggregates per gram (g) of targeted tissue when at least 0.1 g of the pharmaceutical composition per kilogram (kg) of body weight is injected intravenously (IV) or intraarterially (IA) into said subject.

7 Claims, 4 Drawing Sheets

PHARMACEUTICAL COMPOSITION COMPRISING NANOPARTICLES, PREPARATION AND USES THEREOF

CROSS-REFERENCE TO RELATED APPLICATION

This application is the U.S. national stage application of International Patent Application No. PCT/EP2014/078619, filed Dec. 19, 2014.

FIELD OF THE INVENTION

The present application relates to a pharmaceutical composition comprising biocompatible nanoparticles or nanoparticles aggregates which allows the appropriate delivery of said biocompatible nanoparticles or nanoparticles aggregates to a target site in a subject in need thereof. The appropriate delivery is a systematic delivery to the target site which occurs in a dosage range ensuring an acceptable benefit/risk ratio of the treatment induced by the pharmaceutical composition for the subject. The composition indeed allows an accumulation of the biocompatible nanoparticles or nanoparticles aggregates into the targeted tissue of the subject of at least 4 milligrams (mg) nanoparticles or nanoparticles aggregates per gram (g) of targeted tissue when at least 0.1 g of the pharmaceutical composition per kilogram (kg) of body weight is injected intravenously (IV) or intraarterially (IA) into said subject.

BACKGROUND

According to the European Technology Platform of Nanomedicine, nanomedicine is defined "as the application of Nanotechnology to Health. It exploits the improved and often novel physical, chemical, and biological properties of materials at the nanometric scale. Nanomedicine has potential impact on the prevention, early and reliable diagnosis and treatment of diseases."

In the context of therapeutic use, in order to ensure an acceptable benefit/risk ratio of the treatment, the delivery of nanomaterials to the target site in the appropriate dosage range is of utmost importance.

Nanoparticles physicochemical parameters, such as their composition, size, core properties, surface modifications (pegylation and surface charge) and targeting ligand functionalization, impact on nanoparticles interactions with biological barriers. All the above listed factors have been shown to substantially affect the biodistribution and blood circulation half-life of circulating nanoparticles by reducing the level of nonspecific uptake, delaying opsonization, and increasing the extent of tissue specific accumulation. Particularly, nanoparticles surface functionalization has been used to increase residence time in the blood and reduce nonspecific distribution. For instance, it is well established that hydrophilic polymers, most notably poly(ethylene glycol) (PEG), can be grafted, conjugated, or adsorbed on the surface of nanoparticles to form the corona, which provides steric stabilization and confers "stealth" properties such as prevention of protein adsorption. In general, pegylated nanoparticles were found to have longer circulation times and higher levels of tumor accumulation than nonpegylated nanoparticles. Moreover, the chain length, shape, and density of PEG on the particle surface have been shown to be the main parameters affecting nanoparticle surface phagocytosis.

Notably, Gref et al. have systematically studied the effect of PEG chain length in preventing protein adsorption on the surface of nanoparticles. Their results showed that an optimal molecular mass (Mw) range exists (between 2 and 5 kDa) in order to reduce plasma protein adsorption of their PLA-PEG nanoparticles. The most significant reduction of protein adsorption was found for pegylated particles (5 wt %). Interestingly, a threshold of 1-2 nm space between the PEG chains was estimated for minimal protein adsorption.

Similarly, C. Fang et al. have shown the effect of the molecular mass of PEG for passive targeting of stealth poly(cyanoacrylate-co-n-hexadecyl) cyanoacrylate (PH-DCA) nanoparticles. PEG 10 kDa was found to be the most efficient size of PEG as compared to PEG 2 kDa and PEG 5 kDa in preventing protein adsorption.

In summary, much has been learned about PEG molecular mass and PEG density of nanoparticles which has led to reduced plasma protein adsorption, opsonization, and non-specific uptake. In turn, this has resulted in increased nanoparticle circulation half-life and improved therapeutic efficacy of drugs delivered using pegylated nanocarriers.

However, there is still a need for a composition capable of ensuring systematic delivery of the nanoparticles it contains to a target site in the appropriate dosage range in order to ensure an acceptable benefit/risk ratio of the treatment induced by said composition for the subject.

SUMMARY OF THE INVENTION

Inventors now herein disclose a pharmaceutical composition comprising nanoparticles or nanoparticles aggregates allowing the systematic delivery of the nanoparticles or nanoparticles aggregates to a target site, preferably to a tumor site, in the appropriate dosage range, i.e. in the dosage range ensuring an acceptable benefit/risk ratio of the treatment induced by the pharmaceutical composition for the subject, as accepted by physicians.

The pharmaceutical composition according to the invention comprises a biocompatible nanoparticles or nanoparticles aggregates wherein i) each of said biocompatible nanoparticle or nanoparticles aggregate is covered with at least one biocompatible hydrophilic polymer, ii) the longest dimension of each of the biocompatible nanoparticle or nanoparticles aggregate is between about 50 nm and about 150 nm, preferably between about 60 nm and about 100 nm, even more preferably between about 60 nm and about 90 nm, iii) the surface charge value of each of the biocompatible nanoparticle or nanoparticles aggregate is between −15 mV and +15 mV when measured in an aqueous medium at pH 6-8, and iv) said biocompatible nanoparticles or nanoparticles aggregates have, when administered to a subject in need thereof, an accumulation factor (Accu F) in a targeted tissue of the subject of at least 260500, said Accu F being defined by the equation:

$$\text{Accu } F = \sqrt{(d*\text{Mw})} * C^2,$$

wherein:

d is the compactness of the at least one biocompatible hydrophilic polymer covering the surface of each of said nanoparticle or nanoparticles aggregate expressed as the number of molecules per $nm^2$ of surface, or when at least two distinct polymers are covering the surface of each of said nanoparticle or nanoparticles aggregate, d is the compactness of the biocompatible hydrophilic polymer exhibiting the highest molecular weight Mw is the molecular weight of the at least one biocompatible hydrophilic polymer expressed in Kilodalton (kDa), and C is the concentration of the nanoparticles or nanoparticles aggregates in the pharmaceutical composition expressed in g/L, and said Accu F allowing an accumulation of the biocompatible nanoparticles or nanoparticles aggregates of the pharmaceutical composition into the targeted tissue of the subject of at least 4 milligrams (mg) nanoparticles or nanoparticles aggregates per gram (g) of targeted tissue when at least 0.1 g of the pharmaceutical composition per kilogram (kg) of body weight is injected intravenously (IV) or intraarterially (IA) into the subject.

In a typical embodiment, the herein described pharmaceutical composition is for use for altering or destroying cells of the targeted tissue of the subject when said cells are exposed to ionizing radiations.

In a particular embodiment, each of the biocompatible nanoparticle or nanoparticles aggregate present in the pharmaceutical composition is covered with at least two biocompatible hydrophilic polymers. In such circumstances, d and Mw are the compactness and the molecular weight respectively of the biocompatible hydrophilic polymer of said at least two biocompatible hydrophilic polymers which exhibits the highest molecular weight.

DETAILED DESCRIPTION OF THE INVENTION

In the present description, the terms "nanoparticle(s)", "nanoparticles aggregate(s)" and "particle(s)" are indifferently used.

In the context of the present invention, the terms "nanoparticle" or "nanoparticles aggregate" refer to a product, in particular a synthetic product, with a size in the nanometer range, typically between 1 nm and 500 nm.

The term "aggregate of nanoparticles" or "nanoparticles aggregate" refers to an assemblage of nanoparticles strongly, typically covalently, bound to each other.

The terms "size of the nanoparticle" or "size of the nanoparticles aggregate" and "largest size of the nanoparticle" or "largest size of the nanoparticles aggregate" herein refer to the "largest dimension of the nanoparticle" or "largest dimension of the nanoparticles aggregate" or "diameter of the nanoparticle" or "diameter of the nanoparticles aggregate".

Transmission Electron Microscopy (TEM) can be used to measure the size of the nanoparticle or nanoparticles aggregate. As well, Dynamic Light Scattering (DLS) can be used to measure the hydrodynamic diameter of nanoparticles or nanoparticles aggregates in solution. A preferred method is DLS (Ref. International Standard ISO22412 Particle Size Analysis—Dynamic Light Scattering, International Organisation for Standardisation (ISO) 2008). These two methods may also be used one after the other to compare size measurements and confirm said size. The size of a nanoparticle or nanoparticles aggregate is typically measured when the nanoparticle or nanoparticles aggregate is coated with the at least one biocompatible hydrophilic polymer.

The largest dimension of a nanoparticle or nanoparticles aggregate as herein defined is typically between about 5 nm and about 250 nm, preferably between about 10 nm and about 200 nm or about 100 nm, more preferably between about 20 nm and about 150 nm, even more preferably between about 50 and about 150 nm, or between about 60 nm and about 100 nm or between about 60 nm and about 90 nm.

As the shape of the particle can influence its "biocompatibility", particle having a quite homogeneous shape is preferred. For pharmacokinetic reasons, nanoparticles or nanoparticles aggregates being essentially spherical, round or ovoid in shape are thus preferred. Such a shape also favors the nanoparticle or nanoparticles aggregate interaction with or uptake by cells. Spherical or round shape is particularly preferred. Typically, the largest dimension is the diameter of a nanoparticle or nanoparticles aggregate of round or spherical shape, or the longest length of a nanoparticle or nanoparticles aggregate of ovoid or oval shape.

The nanoparticle usable in the context of the invention can be either organic or inorganic. A mixture of organic and inorganic nanoparticles can further be used.

When organic, the nanoparticle can be a lipid-based nanoparticle (glycerolipid, phospholipid, sterol lipid, etc.), a protein-based nanoparticle, also herein identified as "protein-nanoparticle" (albumin, for instance), a polymer-based nanoparticle ("polymeric nanoparticle"), a co-polymer-based nanoparticle ("co-polymeric nanoparticle"), a carbon-based nanoparticle, or a virus-like nanoparticle (for example, a viral vector).

The organic nanoparticle may further be a nanosphere (plain nanoparticle) or a nanocapsule (hollow nanoparticle) such as a liposome, a gel, a hydrogel, a micelle, a dendrimer, etc. A mixture of the herein described organic nanoparticles can also be used.

The polymer or co-polymer can be of natural or synthetic origin. Examples of synthetic (artificial) and natural polymers or co-polymers usable in the context of the invention to prepare organic nanoparticles can be selected from polylactic acid (PLA), Poly (lactide-co-glycolic) acid (PLGA), Polyethyleneglycol (PEG), Polyglactin, Polylactide, Polyoxyethylene fatty acid esters, Polypropylene glycol, Polysorbate, Polyvinyl alcohol, Polyacrylamide, Polymethylmethacrylate, Polyalkylcyanoacrylate, Polylactate-coglycolate, Poly(amido amine), Poly(ethyleneimine), alginate, cellulose and cellulose derivative polymers, collagen, hyaluronic acid, polyglutamic acid (PGA), actin, polysaccharide, and gelatin. The organic nanoparticle may be a drug carrier nanoparticle.

When inorganic the nanoparticle and/or nanoparticles aggregate may be made of any inorganic material. The inorganic material may for example comprise metallic element from period 3, 4, 5, 6 of the Mendeleev periodic table, including the lanthanides.

The inorganic material the nanoparticle or nanoparticles aggregate is prepared with, typically comprises, at least one metal element, typically a metal element having an atomic number Z of at least 25. The inorganic material can also comprise several metal elements, typically two metal elements. In a particular embodiment the nanoparticle or nanoparticles aggregate consists of an inorganic material, said inorganic material comprising a single metal element or a mixture of metal elements.

The inorganic material is preferably a material having an effective atomic number ($Z_{eff}$) of at least 25, preferably at least 40 or 41, more preferably at least 50 or 51, more preferably at least 60, 61, 62 or even 63.

Effective atomic number is a term that is similar to atomic number but is used for compounds (e.g. water) and mixtures of different materials (such as tissue and bone) rather than for atoms. Effective atomic number calculates the average atomic number for a compound or mixture of materials. It is abbreviated $Z_{eff}$.

The effective atomic number is calculated by taking the fractional proportion of each atom in the compound and multiplying that by the atomic number of the atom. The formula for the effective atomic number, $Z_{eff}$, is as follows:

$$Z_{eff} = \sqrt[2.94]{f_1 \times (Z_1)^{2.94} + f_2 \times (Z_2)^{2.94} + f_3 \times (Z_3)^{2.94} + \ldots}$$

where fn is the fraction of the total number of electrons associated with each element, and Zn is the atomic number of each element.

The atomic number (also known as the proton number) is the number of protons found in the nucleus of an atom. It is traditionally represented by the symbol Z (and is herein also identified as Zn). The atomic number uniquely identifies a chemical element. In an atom of neutral charge, atomic number is equal to the number of electrons.

An example is that of water ($H_2O$) which is made up of two hydrogen atoms (Z=1) and one oxygen atom (Z=8). The total number of electrons is 1+1+8=10. The fraction of electrons corresponding to the two hydrogens is 2/10 and the fraction of electrons corresponding to the unique oxygen is (8/10). $Z_{eff}$ of water is therefore:

$$Z_{eff} = \sqrt[2.94]{0.2 \times 1^{2.94} + 0.8 \times 8^{2.94}} = 7.42$$

$Z_{eff}$ participate to the incoming radiations absorption capacity of nanoparticles.

The inorganic material constituting the nanoparticle and/or nanoparticles aggregate is typically selected from a metal, an oxide, a sulfide and any mixture thereof. Typically this inorganic material comprises at least one metal element having an atomic number Z of at least 25.

When the inorganic material constituting the nanoparticle and/or nanoparticles aggregate is an oxide, this oxide may be selected for example from iron oxide ($Fe_3O_4$ or $Fe_2O_3$), zirconium oxide ($ZrO_2$), cerium (IV) oxide ($CeO_2$), neodynium (III) oxide ($Nd_2O_3$), samarium (III) oxide ($Sm_2O_3$), europium (III) oxide ($Eu_2O_3$), gadolinium (III) oxide ($Gd_2O_3$), terbium (III) oxide ($Tb_2O_3$), dysprosium (III) oxide ($Dy_2O_3$), holmium oxide ($Ho_2O_3$), erbium oxide ($Er_2O_3$), thullium (III) oxide ($Tm_2O_3$), ytterbium oxide ($Yb_2O_3$), lutetium oxide ($lu_2O_3$), hafnium (IV) oxide ($HfO_2$), tantalum (V) oxide ($Ta_2O_5$), rhenium (IV) oxide ($ReO_2$), and bismuth (III) oxide ($Bi_2O_3$). In a preferred embodiment the inorganic material constituting the nanoparticle and/or nanoparticles aggregate is $HfO_2$. In a particular embodiment, a mixture of oxides can also be used as the inorganic material to prepare the nanoparticle and/or nanoparticles aggregate of the invention. Nanoparticle and/or nanoparticles aggregate of the invention can thus comprise or consist of a mixture of oxides.

When the inorganic material constituting the nanoparticle and/or nanoparticles aggregate is a metal, this metal may be selected for example from gold metal (Au), silver metal (Ag), platinum metal (Pt), palladium metal (Pd), tin metal (Sn), tantalum metal (Ta), ytterbium metal (Yb), zirconium metal (Zr), hafnium metal (Hf), terbium metal (Tb), thulium metal (Tm), cerium metal (Ce), dysprosium metal (Dy), erbium metal (Er), europium metal (Eu), holmium metal (Ho), iron metal (Fe), lanthanum metal (La), neodymium metal (Nd), praseodymium metal (Pr), and lutetium metal (Lu). In a preferred embodiment the metal is gold.

As indicated previously, in a particular embodiment, a mixture of metals can also be used as the inorganic material to prepare the nanoparticle and/or nanoparticles aggregate of the invention.

Nanoparticle and/or nanoparticles aggregate of the invention can thus comprise or consist of a mixture of metals.

When the inorganic material constituting the nanoparticle and/or nanoparticles aggregate is a sulfide, this sulfide may be selected for example from silver sulfide ($Ag_2S$), bismuth sulfide ($Bi_2S_3$), and iron sulfide ($Fe_3S_4$). In a particular embodiment, a mixture of sulfides can also be used to prepare the nanoparticle and/or nanoparticles aggregate of the invention.

Nanoparticle and/or nanoparticles aggregate of the invention can thus comprise or consist of a mixture of sulfides.

A mixture of an oxide, of a metal and/or of a sulfide can also be used to prepare the nanoparticles and/or nanoparticles aggregates of the invention. Nanoparticle and/or nanoparticles aggregate of the invention can thus comprise or consist of a mixture of an oxide, a metal and/or a sulfide. An example of a nanoparticle which can advantageously be used in the context of the present invention is a gold metal nanoparticle covered with hafnium oxide material.

In a particular embodiment, the nanoparticle or nanoparticle aggregate consists of an inorganic material, wherein the density of said nanoparticle and nanoparticle aggregate is of at least 7 g/cm$^3$ (WO 2009/147214).

In a particular embodiment, the nanoparticle or nanoparticle aggregate consisting of an inorganic material may be a drug carrier nanoparticle.

In a preferred embodiment, the nanoparticle and/or nanoparticles aggregate used in the context of the present invention to prepare a composition of interest can be coated with a biocompatible hydrophilic polymer. Indeed, when the nanoparticles of the present invention are administered to a subject via the intravenous (IV) or intraarterial (IA) route, a biocompatible coating with a material selected from a biocompatible hydrophilic polymer is particularly advantageous to optimize the biodistribution of the nanoparticles.

The biocompatible hydrophilic coating can be made of one or more biocompatible hydrophilic polymer. These polymers can be positively or negatively charged as far as the surface charge value of each of the biocompatible nanoparticle or nanoparticles aggregates is between −15 mV and +15 mV when measured in aqueous medium at pH 6-8.

This charge can be determined by zeta potential measurements, typically performed on nanoparticle suspensions the concentrations of which vary between 0.2 and 10 g/L, the nanoparticles being suspended in an aqueous medium with a pH between 6 and 8, and typically for electrolyte concentrations in the aqueous medium between 0.001 and 0.2 M, for example of 0.01 M or 0.15 M.

These biocompatible hydrophilic polymers can be selected from the group consisting of polyethylene glycol (PEG), polyglycerol, polyethylene oxide, polyvinyl alcohol such as polyvinylpyrrolidone, polymethylmethacrylate, polyacrylate, polyacrylamide such as poly(N-isopropylacrylamide), polyetheretherketone, polycarbamide, polysaccharides such as dextran, sulfate dextran, chitosan, alginate, xylan, hyaluronic acid or β-Glucan, proteins such as collagen, polyglutamic acid, polylysine or albumin. In a preferred embodiment the biocompatible hydrophilic polymer is PEG.

These biocompatible hydrophilic polymers can also be selected from the group consisting of co-polymers such as poloxamers, poly(lactic-co-glycolic acid) or N-(2-Hydroxypropyl) methacrylamide or a combination of the different polymers or co-polymers mentioned above.

The biocompatible coating allows in particular the nanoparticle stability in a fluid, such as a physiological fluid (blood, plasma, serum, etc.), any isotonic media or physiologic medium, for example media comprising glucose (5%) and/or NaCl (0.9%), which is required for a pharmaceutical administration.

Stability may be confirmed by dry extract quantification using a drying oven and measured on a nanoparticle suspension prior to and after filtration, typically on a 0.22 or 0.45 µm filter.

Advantageously, the coating preserves the integrity of the particle in vivo, ensures or improves the biocompatibility thereof, and facilitates an optional functionalization thereof (for example with spacer molecules, targeting agents, proteins, etc.). The hydrophilic biocompatible polymer can be grafted and/or conjugated (via alcoxysilane groups on an oxide nanoparticle, or via a thiol group on a metal nanoparticle for instance), and/or adsorbed (via electrostatic or hydrogen interaction for instance) to the surface of the nanoparticles or nanoparticles aggregates.

In a particular embodiment, the biocompatible hydrophilic polymer is grafted and/or conjugated on the oxide nanoparticle's surface via an alcoxysilane group.

In another particular embodiment, the biocompatible hydrophilic polymer is grafted and/or conjugated on the metallic nanoparticle's surface via a thiol group.

When the nanoparticle or nanoparticles aggregate is an oxide nanoparticle or nanoparticles aggregate, the hydrophilic biocompatible polymer can typically be an alkoxysilane functionalized polyethylene glycol or polyethylene oxide such as a [methoxy(polyethyleneoxy)propyl]alkoxysilane with a molecular weight (expressed in kDa) comprised between 0.4 kDa and 30 kDa, more preferably between 2 kDa and 20 kDa or between 5 kDa and 20 kDa, for example equal to 10 kDa.

For example, when the nanoparticle or nanoparticles aggregate is a hafnium oxide nanoparticle or nanoparticles aggregate, the hydrophilic biocompatible polymer can be a 2-[Methoxy(polyethyleneoxy)propyl]triethoxysilane (mPEG silane) with a molecular weight of 10 kDa or 20 kDa.

When the nanoparticle or nanoparticles aggregate is a hafnium oxide nanoparticle or nanoparticles aggregate and when at least two distinct hydrophilic biocompatible polymers are used, these polymers can typically be 2-[Methoxy(polyethyleneoxy)propyl]triethoxysilane the molecular weights of which are of 0.45 kDa and 10 kDa, respectively, or of 0.45 kDa and 20 kDa, respectively.

Another particular object herein described relates to a pharmaceutical composition comprising nanoparticles such as defined hereinabove, preferably together with a pharmaceutically acceptable carrier or vehicle. The composition is typically in the form of a liquid (particles in suspension).

The carrier which is employed can be any classical support for the skilled person, such as a saline, isotonic, sterile, buffered solution, a non-aqueous vehicle solution and the like.

The composition can also comprise stabilizers, sweeteners, surfactants, polymers and the like.

It can be formulated for example as ampoule, bottle or prefilled syringe by using techniques of pharmaceutical formulation known by the skilled person.

Generally, the composition comprises between about 0.05 g/L and about 450 g/L of nanoparticles, preferably at least about 10 g/L, 20 g/L, 40 g/L, 45 g/L, 50 g/L, 55 g/L, 60 g/L, 80 g/L, 100 g/L, 150 g/L, 180 g/L, 200 g/L, 250 g/L, 300 g/L, 350 g/L, 360 g/L or 400 g/L of nanoparticles.

The concentration of nanoparticles in the composition can be measured by dry extract. A dry extract is ideally measured following a drying step of the suspension comprising the nanoparticles in a drying oven.

The nanoparticles of the invention can be administered to the subject using different possible routes such as intra-arterial (IA), subcutaneous, intra venous (IV), intra-dermic, intra peritoneal, intra-thecal, intra-ocular or oral route (per os), preferably using IV or IA.

Repeated injections or administrations of nanoparticles can be performed, when appropriate.

The nanoparticles or nanoparticles aggregates of the invention can be used in many fields, particularly in human or veterinary medicine. Nanoparticles or nanoparticles aggregates and compositions according to the invention, as herein described, are preferably for use in an animal, preferably in a mammal (for example in the context of veterinary medicine), even more preferably in a human being, as a therapeutic agent.

In a particular embodiment, nanoparticles or nanoparticles aggregates and compositions according to the invention, as herein described, are for use in particular in oncology, preferably when the nanoparticle is exposed to ionizing radiations.

The invention can be used to treat any type of malignant solid tumors, in particular of epithelial, neuroectodermal or mesenchymal origin, as well as lymphatic cancers. The nanoparticles and/or nanoparticles aggregates can also be used for advanced stage tumors which cannot be surgically removed.

The nanoparticles and/or nanoparticles aggregates herein described are in particular intended to be used to treat cancer where radiotherapy is a classical treatment or is the most appropriate treatment for a particular subject, or where radiotherapy could be indicated. Such cancer may be selected in particular from the group consisting of skin cancer, including malignant neoplasms associated with AIDS, melanoma; squamous cancer; central nervous system tumors including brain, cerebellum, pituitary, spinal cord, brainstem, eye and orbit; head and neck tumors; lung cancers; breast cancers; gastrointestinal tumors such as liver and hepatobiliary tract cancers, colon, rectum and anal cancers, stomach, pancreas, oesophagus cancer; male genitourinary tumors such as prostate, testis, penis and urethra cancers; gynecologic tumors such as uterine cervix, endometrium, ovary, fallopian tube, vagina and vulvar cancers; adrenal and retroperitoneal tumors; sarcomas of bone and soft tissue regardless of the localization; and pediatric tumors such as Wilms' tumor, neuroblastoma, central nervous system tumors, Ewing's sarcoma, etc.

In a particular embodiment, the present invention relates to a method of accumulating in a subject suffering from a cancer more than about 4 mg of nanoparticles and/or nanoparticles aggregates per gram of targeted tissue, more preferably of tumor tissue, for example more than about 5 mg/g, preferably more than about 6 mg/g of nanoparticles and/or nanoparticles aggregates. This method comprises a step of administering to a subject at least 0.1 g/kg, at least 0.2 g/kg, at least 0.3 g/kg, at least 0.4 g/kg, or at least 0.5 g/kg, for example at least 0.8 g/kg or at least 1 g/kg of the pharmaceutical composition by IA or IV route, said pharmaceutical composition comprising nanoparticles and/or nanoparticles aggregates, wherein i) each of said biocompatible nanoparticle or nanoparticles aggregate is covered with at least one biocompatible hydrophilic polymer, ii) the longest dimension of each of the biocompatible nanoparticle or nanoparticles aggregate is between about 50 nm and about 150 nm, preferably between about 60 nm and about 100 nm, even more preferably between about 60 nm and about 90 nm, iii) the surface charge value of each of the biocompatible nanoparticle or nanoparticles aggregate is between −15 mV and +15 mV when measured in an aqueous medium at pH 6-8, and iv) said biocompatible nanoparticles or nanoparticles aggregates have, when administered to a subject in need thereof, an accumulation factor (Accu F) in a targeted tissue of the subject of at least 260500, said Accu F being defined by the equation:

$$Accu\ F = \sqrt{(d*Mw)} * C^2,$$

wherein:

d is the compactness of the at least one biocompatible hydrophilic polymer covering the surface of each of said nanoparticle or nanoparticles aggregate expressed as the number of molecule per $nm^2$ of surface, or when at least two distinct polymers are covering the surface of each of said nanoparticle or nanoparticles aggregate, d is the compactness of the biocompatible hydrophilic polymer exhibiting the highest molecular weight, Mw is the molecular weight of the at least one biocompatible hydrophilic polymer expressed in Kilodalton (kDa), and C is the concentration of the nanoparticles or nanoparticles aggregates in the pharmaceutical composition expressed in g/L.

As explained previously the subject can be a human being, the body weight of the human being comprised between 50 and 100 Kg, typically between 50 and 70 Kg.

When inorganic, the accumulation of nanoparticles or nanoparticles aggregates of the invention at the target site, preferably at the tumor site can typically be measured using a computed tomography (CT) imaging technique. The inorganic nanoparticles as herein described used to prepare the composition will create a marked contrast in the CT images due to the difference of electron density between the targeted tissue and the nanoparticles.

The Hounsfield number is a normalized value of the calculated X-ray absorption coefficient of a pixel (picture element) in a computed tomogram, expressed in Hounsfield units (HU), where the CT number of air is −1000 (HU=−1000) and that of water is zero (HU=0). For inorganic nanoparticles with high electron density, separation between tissues and nanoparticles occurs typically around HU values of 120 or above. Above HU values of typically 120 up to 200, no more soft tissue densities can be found. A histogram corresponding to the distribution of HU values above typically 120 or 200 is established. The histogram represents the occurrences of voxels related to specific HU values above a specific threshold, typically 120 HU or 200 HU. The mean HU value for the distribution of nanoparticles is obtained using the following equation:

$$Mean\ HU = \Sigma(HU \times occurence)/\Sigma occurences$$

A calibration curve is used where the Hounsfield number (HU) is plotted against an increased concentration of the nanoparticles in liquid suspension. From the calibration curve, a mean concentration of nanoparticles is calculated (Xmean in g/L).

When inorganic, the accumulation of nanoparticles or nanoparticles aggregates of the invention at the target site, preferably at the tumor site may also be measured by quantification of the metallic elements constituting the nanoparticles using the ICP-MS (Inductively Coupled Plasma-Mass Spectrometry) or ICP-OES (Inductively Coupled Plasma-Optical Emission Spectrometry) technique.

When organic, the accumulation of nanoparticles or nanoparticles aggregates of the invention at the target site, preferably at the tumor site may typically be measured by imaging techniques using fluorescent probes.

When nanoparticles and nanoparticles aggregates are inorganic nanoparticles and nanoparticles aggregates, ionizing radiations includes typically X-Rays, gamma-Rays, UV-Rays, electron beams as well as particle beams of, for example neutrons, carbon ions and protons.

Under the effect of ionizing radiations, in particular X-Rays, gamma-rays, radioactive isotopes and/or electron beams, the nanoparticles and/or nanoparticles aggregates are activated, and produce electrons and/or high energy photons. Those electrons and/or high energy photons emitted after ionization will be involved in the direct and/or indirect cell damage, possibly via free radicals generation, and ultimately for cell destruction, resulting in a better outcome for the patient. Surprisingly, inventors discovered that the accumulation of the nanoparticles in the targeted tissues, preferably at the tumor site, which is equal to or above 4 mg/g, is responsible for a markedly increased efficiency of the radiotherapy when compared to radiotherapy alone.

The particles can be excited within a large range of total dose of radiations. Amounts and schedules (planning and delivery of irradiations whichever fraction close, fraction delivery schema, total close alone or in combination with other anticancer agents, etc.) is defined for any disease/anatomical site/disease stage patient setting/patient age (children, adult, elderly patient), and constitutes the standard of care for any specific situation.

The irradiation can be applied at any time after administration of the nanoparticles, on one or more occasions, by using any currently available system of radiotherapy or radiography. As indicated previously, appropriate radiations or sources of excitation are preferably ionizing radiations and can advantageously be selected from the group consisting of X-Rays, gamma-Rays, electron beams, ion beams and radioactive isotopes or radioisotope emissions. X-Rays is a particularly preferred source of excitation.

Ionizing radiations are typically of about 2 KeV to about 25 000 KeV, in particular of about 2 KeV to 30 about 6000 KeV (i.e. 6 MeV) (LINAC source), or of about 2 KeV to about 1500 KeV (such as a cobalt 60 source).

In general and in a non-restrictive manner, the following X-Rays can be applied in different cases to excite the particles:

Superficial X-Rays of 2 to 50 keV: to excite nanoparticles near the surface (penetration of a few millimeters);

X-Rays of 50 to 150 keV: in diagnostic but also in therapy;

X-Rays (ortho voltage) of 200 to 500 keV which can penetrate a tissue thickness of 6 cm;

X-Rays (mega voltage) of 1000 keV to 25,000 keV.

Radioactive isotopes can alternatively be used as an ionizing radiation source (named as curietherapy or brachytherapy). In particular, Iodine $^{125}I$ (t ½=60.1 days), Palladium $^{103}Pd$ (t ½=17 days), Cesium $^{137}Cs$, Strontium $^{89}Sr$ (t ½=50.5 days), Samarium $^{153}Sm$ (t ½=46.3 hours), and Iridium $^{192}Ir$ can advantageously be used.

Charged particles such as proton beams, ion beams such as carbon, in particular high energy ion beams, can also be used as an ionizing radiation source and/or neutron beams.

Electron beams may also be used as an ionizing radiation source with energy comprised between 4 MeV and 25 MeV.

Specific monochromatic irradiation sources could be used for selectively generating X-ray radiation at energy close to or corresponding to the desired X-ray absorption edge of the atoms constituting the metallic material.

Preferentially sources of ionizing radiations may be selected from Linear Accelerator (LINAC), Cobalt 60 and brachytherapy sources.

BRIEF DESCRIPTION OF THE DRAWINGS

The quantity of nanoparticle at the tumor site is expressed in mg of nanoparticles per g of tumor (mg/g of tumor). The amount (accumulation) of nanoparticles or nanoparticles aggregate at the tumor site is measured by quantification of the hafnium element by ICP-MS (Inductively Coupled Plasma Mass Spectrometry) and plotted versus the accumulation factor values (Accu F), where Accu $F=\sqrt{(d \times Mw)} \times C^2$, wherein.

d is the compactness of the at least one biocompatible hydrophilic polymer covering the surface of each of said nanoparticle or nanoparticles aggregate expressed as the number of molecules per $nm^2$ of surface, or when at least two distinct polymers are covering the surface of each of said nanoparticle or nanoparticles aggregate, d is the compactness of the biocompatible hydrophilic polymer exhibiting the highest molecular weight.

Mw is the molecular weight of the at least one biocompatible hydrophilic polymer expressed in Kilodalton (kDa) (when at least two distinct polymers are covering the surface, Mw is selected as the highest molecular weight), and C is the concentration of the nanoparticles or nanoparticles aggregates in the pharmaceutical composition expressed in g/L.

Twenty four (24) h after a single injection in tail vein of the suspension of nanoparticles from example 1 (nanoparticles or nanoparticles aggregates concentration equal to 360 g/L and volume of injection equal to 10 ml/kg), a single dose of irradiation (10 Gy using a 200 kVp X-ray source) was performed in the NCI-H460-luc2 (human non small cell lung adenocarcinoma) tumor (n=5 per group). The nanoparticles or nanoparticles aggregates have an accumulation factor value equal to 289794 corresponding to a concentration of 4.1 mg of nanoparticles or nanoparticles aggregates per g of tumor (point 1 on FIG. 1).

After a single injection in tail vein of the biocompatible suspension of hafnium oxide nanoparticles from example 4 (nanoparticles or nanoparticles aggregates concentration equal to 360 g/L and volume of injection equal to 10 ml/kg), three doses of 4 Gy of irradiation (3×4 Gy using a 200 kVp X-ray source) were delivered into the NCI-H460-luc2 tumor (n=5 per group), the first close being delivered 24 h after the administration of the suspension of hafnium oxide. The nanoparticles or nanoparticles aggregates have an accumulation factor value equal to 409831 corresponding to a concentration of 5.6 mg of nanoparticles or nanoparticles aggregates per g of tumor (point 2 on FIG. 1).

After a single injection in tail vein of the biocompatible suspension of hafnium oxide nanoparticles from example 3 (nanoparticles or nanoparticles aggregates concentration equal to 360 g/L and volume of injection equal to 10 ml/kg), three doses of 4 Gy of irradiation (3×4 Gy using a 200 kVp X-ray source) were delivered into the NCI-H460-luc2 tumor (n=5 per group), the first close being delivered 24 h after the administration of the suspension of hafnium oxide. The nanoparticles or nanoparticles aggregates have an accumulation factor value equal to 231836 corresponding to a concentration of 2.4 mg of nanoparticles or nanoparticles aggregates per g of tumor (point 3 on FIG. 1).

EXAMPLES

Example 1

Biocompatible suspension of hafnium oxide ($HfO_2$) nanoparticles or nanoparticles aggregates, using 2-[Methoxy (polyethyleneoxy)propyl]triethoxysilane (mPEG silane) 10 kDa as coating agent.

A tetramethylammonium hydroxide (TMAOH) solution is added to 40 g of hafnium chloride ($HfCl_4$) solution. Addition of TMAOH solution is performed until the pH of the final suspension reaches a pH comprised between 7 and 13. A white precipitate is obtained. The precipitate is further transferred into an autoclave and heated at a temperature comprised between 120° C. and 300° C. to perform crystallization. After cooling the suspension is washed with de-ionized water.

A peptization step is performed in order to get a stable suspension of nanoparticles or nanoparticles aggregates.

A water suspension of mPEG silane 10 kDa is then added to the peptized solution. The amount of mPEG Silane 10 kDa added corresponds to a coating compactness of 0.5 mPEG Silane 10 kDa/$nm^2$ of nanoparticles or nanoparticles aggregates surface. Reaction is performed during between 15 h and 24 h then the pH of the suspension is adjusted to a pH comprised between 6 and 8.

For in vivo experiments the suspension is prepared with 5% glucose or NaCl 150 mM.

Example 2

Biocompatible suspension of hafnium oxide ($HfO_2$) nanoparticles or nanoparticles aggregates, using 2-[Methoxy (polyethyleneoxy)propyl]triethoxysilane (mPEG silane) 20 kDa as coating agent.

A tetramethylammonium hydroxide (TMAOH) solution is added to 40 g of $HfCl_4$ solution. Addition of TMAOH solution is performed until the pH of the final suspension reaches a pH comprised between 7 and 13. A white precipitate is obtained. The precipitate is further transferred into an autoclave and heated at a temperature comprised between 120° C. and 300° C. to perform crystallization. After cooling the suspension is washed with de-ionized water.

A peptization step is performed in order to get a stable suspension of nanoparticles or nanoparticles aggregates.

A water suspension of mPEG silane 20 kDa is then added to the peptized solution. The amount of mPEG Silane 20 kDa added correspond to a coating compactness of 0.5 mPEG Silane 20 kDa/nm² of nanoparticles or nanoparticles aggregates surface. Reaction is performed during between 15 h and 24 h then the pH of the suspension is adjusted to a pH comprised between 6 and 8.

For in vivo experiments the suspension is prepared with 5% glucose or NaCl 150 mM.

Example 3

Biocompatible suspension of hafnium oxide (HfO₂) nanoparticles or nanoparticles aggregates, using 2-[Methoxy (polyethyleneoxy)propyl]trimethoxysilane (mPEG silane) 0.45 kDa as coating agent.

A tetramethylammonium hydroxide (TMAOH) solution is added to 40 g of HfCl₄ solution. Addition of TMAOH solution is performed until the pH of the final suspension reaches a pH comprised between 7 and 13. A white precipitate is obtained. The precipitate is further transferred into an autoclave and heated at a temperature comprised between 120° C. and 300° C. to perform crystallization. After cooling the suspension is washed with de-ionized water.

A peptization step is performed in order to get a stable suspension of nanoparticles or nanoparticles aggregates.

A suspension of mPEG silane 0.45 kDa is then added to the peptized solution. The amount of mPEG Silane 0.45 kDa added corresponds to a coating compactness of 8 mPEG Silane 0.45 kDa/nm² of nanoparticles or nanoparticles aggregates surface. Reaction is performed during between 15 h and 24 h then the pH of the suspension is adjusted to a pH comprised between 6 and 8.

For in vivo experiments the suspension is prepared with 5% glucose or NaCl 150 mM.

Example 4

Biocompatible suspension of hafnium oxide (HfO₂) nanoparticles or nanoparticles aggregates, using a mix of 2-[Methoxy(polyethyleneoxy)propyl]trimethoxysilane (mPEG silane) 0.45 kDa and 2-[Methoxy(polyethyleneoxy)propyl]triethoxysilane (mPEG silane) 20 kDa as coating agent.

A tetramethylammonium hydroxide (TMAOH) solution is added to 40 g of HfCl₄ solution. Addition of TMAOH solution is performed until the pH of the final suspension reaches a pH comprised between 7 and 13. A white precipitate is obtained. The precipitate is further transferred into an autoclave and heated at a temperature comprised between 120° C. and 300° C. to perform crystallization. After cooling the suspension is washed with de-ionized water.

A peptization step is performed in order to get a stable suspension of nanoparticles or nanoparticles aggregates.

A suspension of mPEG silane 0.45 kDa is then added to the peptized solution. The amount of mPEG Silane 0.45 kDa added corresponds to a coating compactness of 5 mPEG Silane 0.45 kDa/nm² of nanoparticles or nanoparticles aggregates surface. Reaction is performed during between 15 h and 24 hours. Subsequently, a suspension of mPEG silane 20 kDa is then added to the solution. The amount of mPEG Silane 20 kDa added corresponds to a coating compactness of 0.5 mPEG Silane 20 kDa/nm² of nanoparticles or nanoparticles aggregates surface. Reaction is performed during between 15 h and 24 hours. The pH of the suspension is adjusted to a pH comprised between 6 and 8.

For in vivo experiments the suspension is prepared with 5% glucose or NaCl 150 mM.

Of note, the nanoparticles and nanoparticles aggregates of example 2 and the nanoparticles and nanoparticles aggregates of example 4 show similar accumulation profiles at the tumor site (see table 1). The accumulation at the tumor site depends on:
- compactness of the biocompatible hydrophilic polymer expressed as the number of molecules per nm² of surface of nanoparticles or nanoparticles aggregates, or when at least two distinct polymers are covering the surface of each of said nanoparticle or nanoparticles aggregate of the compactness of the biocompatible hydrophilic polymer exhibiting the highest molecular weight;
- molecular weight of the biocompatible hydrophilic polymer or when at least two distinct polymers are covering the surface, of the highest molecular weight, and
- concentration of said nanoparticles or nanoparticles aggregates in the pharmaceutical composition expressed in g/L.

Example 5

Figure 1:
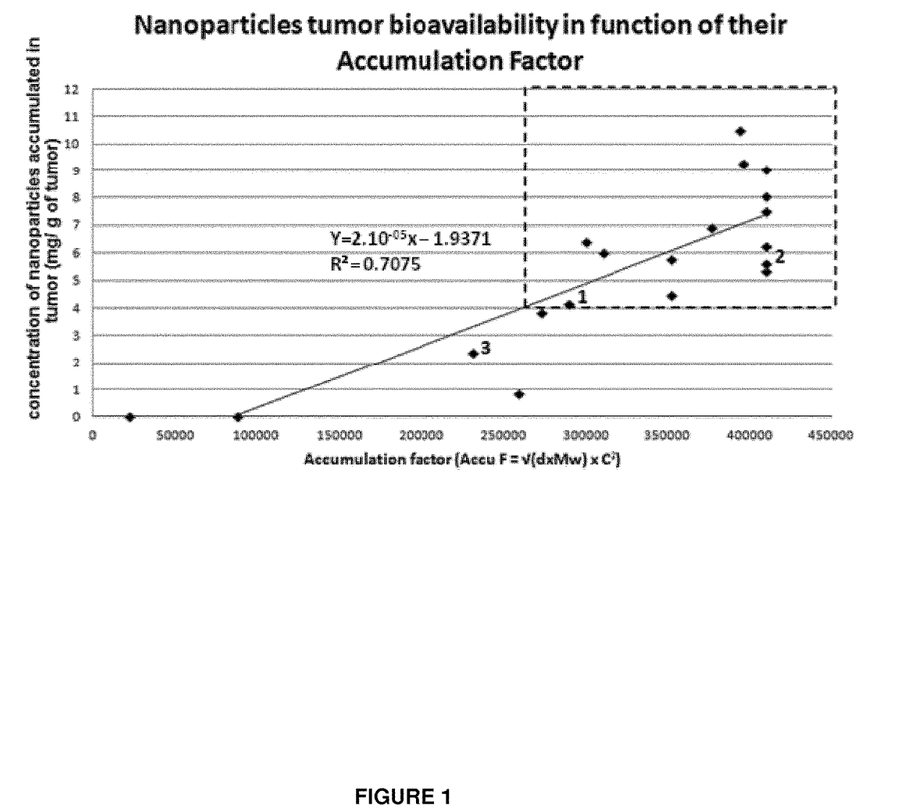
FIG. 1: Nanoparticles or nanoparticles aggregate tumor bioavailability in a panel of tumor model xenografted in nude mice (3 mice per point; see Table 1).

Hafnium oxide nanoparticles and nanoparticles aggregates accumulation at the tumor site following one single intravenous injection of the biocompatible suspension in the tail vein of nude mice xenografted with tumor models (see table 1 and FIG. 1).

Accumulation of hafnium oxide (HfO₂) nanoparticles or nanoparticles aggregates covered with biocompatible hydrophilic polymers (mPEG silane: 2-[Methoxy(polyethyleneoxy)propyl]triethoxysilane) was evaluated using the following human xenografted tumor models in nude mice: NCI-H460-luc2 (human non small cell lung adenocarcinoma), HT1080 (human fibrosarcoma), MDA-MB-231 (human human breast adenocarcinoma), U87 (human glioblastoma multiforme) and LPS80T3 (Liposarcoma patient's fragment). A single intravenous injection of the biocompatible suspension of nanoparticles or nanoparticles aggregates was performed in the tail vein of tumor xenografted nude mice at 10 mL/kg.

At least 24 h after injection mice were sacrificed and tumors were resected. The amount (accumulation) of nanoparticles or nanoparticles aggregates at the tumor site was measured by quantification of the hafnium element by ICP-MS (Inductively Coupled Plasma Mass Spectrometry).

TABLE 1

Hafnium oxide nanoparticles and nanoparticles aggregates accumulation at the tumor site for different tumor models xenografted in nude mice after injection of the suspension of the biocompatible hafnium oxide nanoparticles or nanoparticles aggregates coated with biocompatible mPEG silane hydrophilic polymers. Different values of mPEG silanes compactness (d), molecular weight (Mw) and concentration (C) were tested. Tumor accumulation of nanoparticles or nanoparticles aggregates were evaluated at least 24 h after intravenous injection of the nanoparticles or nanoparticles aggregates suspension by quantification of the hafnium element within the tumor using ICP-MS. When at least two distinct mPEG silanes were covering the surface of each of said nanoparticle or nanoparticles aggregate, d is the compactness of the biocompatible hydrophilic polymer exhibiting the highest molecular weight and Mw is the highest molecular weight.

| tumor model | compactness (d) of mPEG silane exhibiting the highest Mw | Highest molecular weight (Mw) | concentration (C; g/L) | Accumulation factor (Accu F) | tumor accumulation (% Injected dose/g of Tumor) | |
|---|---|---|---|---|---|---|
| HT1080 cell line (human fibrosarcoma) | 10 | 0.45 | 444 | 394272 | 10.5 | |
| NCI-H40-luc2 cell line (human non small cell lung adenocarcinoma) | 10 | 0.45 | 360 | 259200 | 0.9 | |
| NCI-H40-luc2 | 8 | 0.45 | 360 | 231836 | 2.4 | →example 3 (FIG. 1. Dot 3) |
| NCI-H460-luc2 | 0.5 | 10 | 360 | 289794 | 4.1 | →example 1 (FIG. 1. Dot 1) |
| HT1080 | 0.5 | 20 | 294 | 273335 | 3.9 | |
| NCI-H40-luc2 | 0.5 | 20 | 360 | 409831 | 6.2 | →example 2 |
| HT1080 | 0.5 | 20 | 360 | 409831 | 9.1 | |
| NCI-H40-luc2 | 0.5 | 20 | 360 | 409831 | 8.1 | |
| LPS80T3 human tumor fragment (liposarcoma) | 0.5 | 20 | 360 | 409831 | 5.3 | |
| U87MG cell line (glioblastoma) | 0.5 | 20 | 360 | 409831 | 7.5 | |
| NCI-H40-luc2 | 0.5 | 20 | 360 | 409831 | 5.6 | →example 4 (FIG. 1. Dot 2) |
| HT1080 | 0.5 | 20 | 354 | 396284 | 9.3 | |
| HT1080 | 0.5 | 20 | 334 | 352771 | 5.8 | |
| HT1080 | 0.5 | 20 | 308 | 299986 | 6.4 | |
| MDA-MB-231 cell line (breast cancer) | 0.5 | 20 | 334 | 352771 | 4.5 | |
| MDA-MB-232 | 0.5 | 20 | 167 | 88193 | 0.0 | |
| MDA-MB-233 | 0.5 | 20 | 83.5 | 22048 | 0.0 | |
| HT1080 | 0.2 | 30 | 356 | 310439 | 6.0 | |
| HT1080 | 0.4 | 30 | 330 | 377241 | 6.9 | |

Example 6

Figure 2:
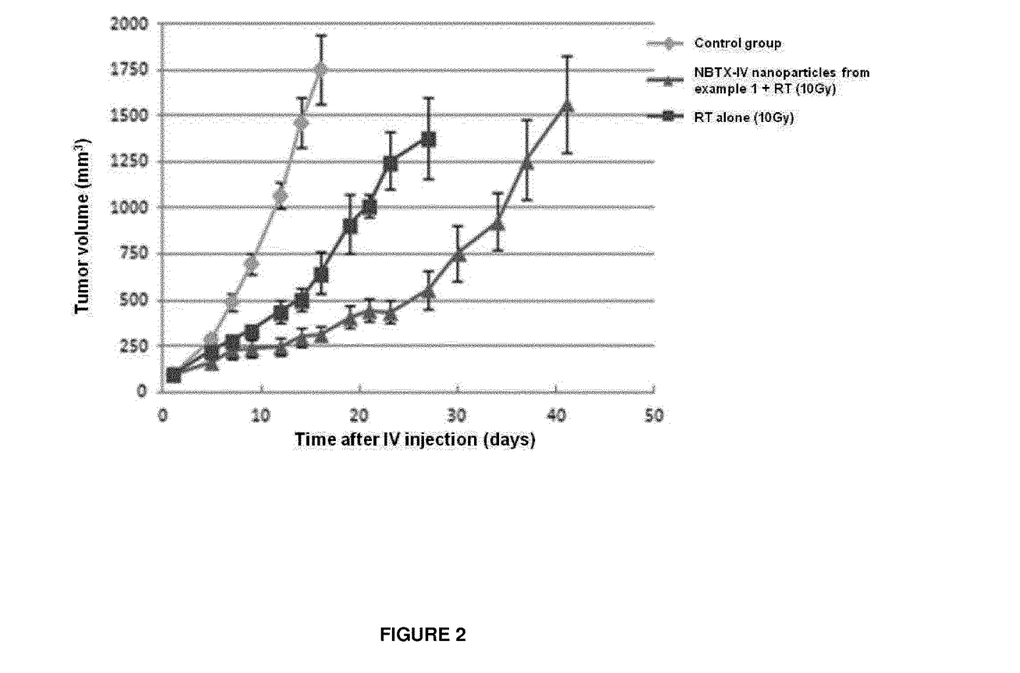
FIG. 2: Anti-tumor efficacy of the biocompatible suspension of hafnium oxide ($HfO_2$) nanoparticles or nanoparticles aggregates from example 1 in an NCI-H460-luc2 tumor model xenografted in nude mice.

Anti-tumor efficacy of the biocompatible suspension of hafnium oxide ($HfO_2$) nanoparticles or nanoparticles aggregates from example 1 in an NCI-H460-luc2 tumor model xenografted in nude mice (see FIG. 2).

Twenty four (24) h after a single injection in tail vein of the suspension of nanoparticles from example 1 (nanoparticles or nanoparticles aggregates concentration equal to 360 g/L and volume of injection equal to 10 ml/kg), a single dose of irradiation (10 Gy using a 200 kVp X-ray source) was performed in the NCI-H460-luc2 (human non small cell lung adenocarcinoma) tumor (n=5 per group). The tumor growth delay curves show a marked anti-tumor efficacy of NBTX-IV nanoparticles activated with radiotherapy when compared to the effect obtained with radiotherapy alone, i.e. in the absence of the biocompatible suspension of $HfO_2$ nanoparticles or nanoparticles aggregates from example 1 (control group) (see FIG. 2). No side effects were observed. The nanoparticles or nanoparticles aggregates have an accumulation factor value equal to 289794 corresponding to a concentration of 4.1 mg of nanoparticles or nanoparticles aggregates per g of tumor (point 1 on FIG. 1).

Example 7

Figure 3:
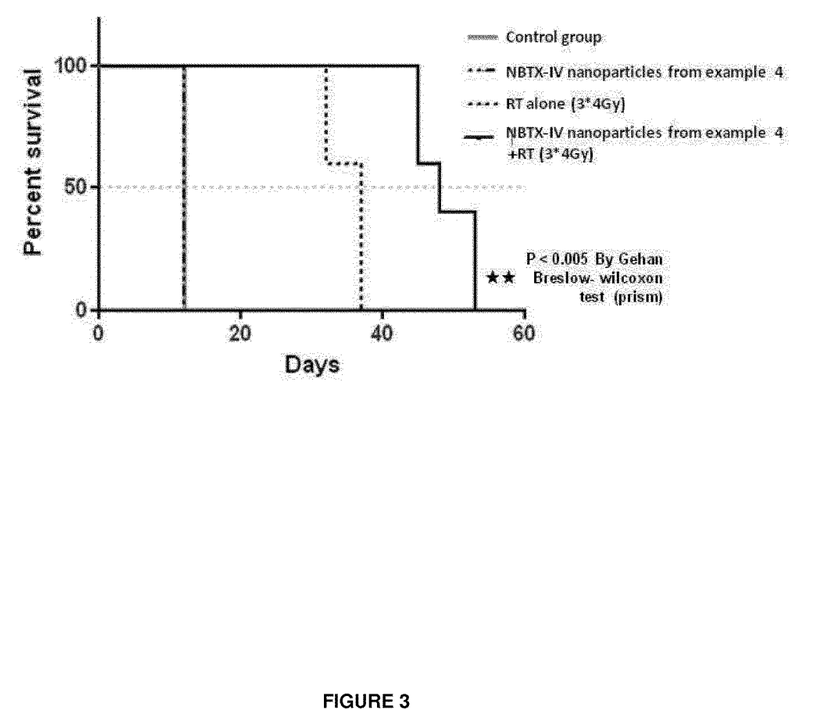
FIG. 3: Anti-tumor efficacy of the biocompatible suspension of hafnium oxide ($HfO_2$) nanoparticles from example 4 in an NCI-11460-luc2 tumor model xenografted on nude mouse.

Anti-tumor efficacy of the biocompatible suspension of hafnium oxide ($HfO_2$) nanoparticles or nanoparticles aggregates from example 4 in an NCI-H460-luc2 tumor model xenografted in nude mice (see FIG. 3).

After a single injection in tail vein of the biocompatible suspension of hafnium oxide nanoparticles from example 4 (nanoparticles or nanoparticles aggregates concentration equal to 360 g/L and volume of injection equal to 10 ml/kg), three doses of 4 Gy of irradiation (3×4 Gy using a 200 kVp X-ray source) were delivered in the NCI-H460-luc2 tumor (n=5 per group), the first close being delivered 24 h after the administration of the suspension of hafnium oxide. No side effects were observed. A significant difference in survival ($P<0.005$) of NBTX-IV nanoparticles activated with radiotherapy was observed when compared to the effect obtained with radiotherapy alone, i.e. in the absence of the biocompatible suspension of $HfO_2$ nanoparticles or nanoparticles aggregates from example 4 (control group) (see FIG. 3). The nanoparticles or nanoparticles aggregates have an accumulation factor value equal to 409831 corresponding to a concentration of 5.6 mg of nanoparticles or nanoparticles aggregates per g of tumor (point 2 on FIG. 1).

Example 8

Figure 4:
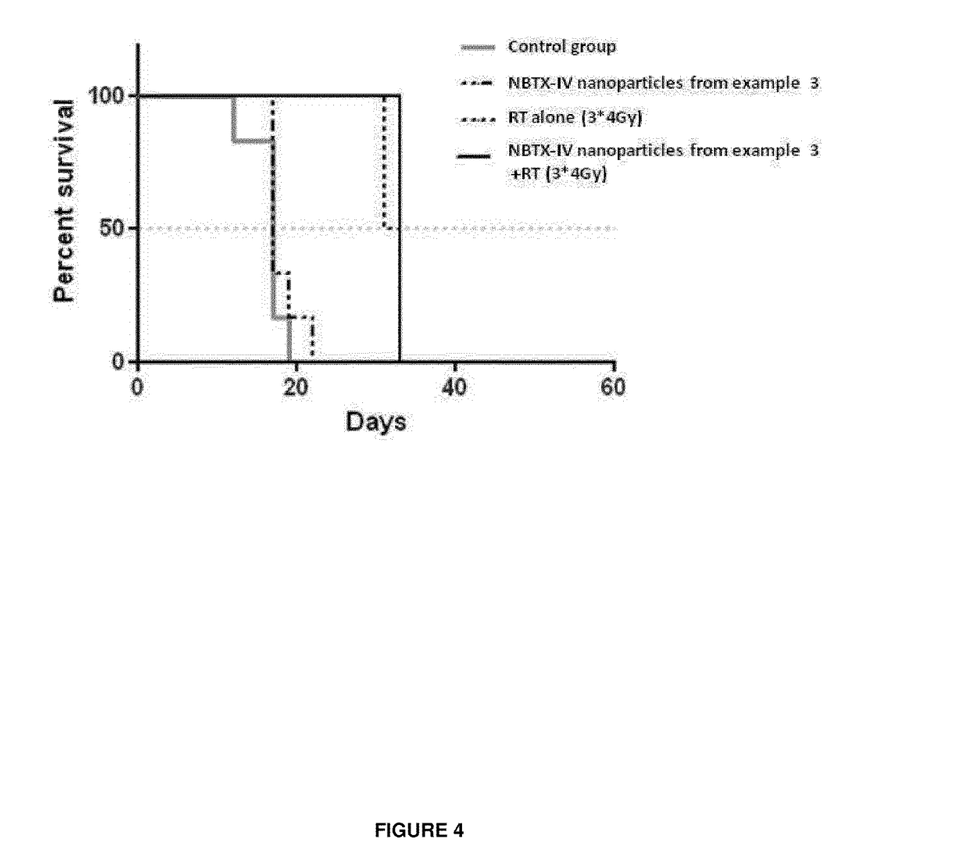
FIG. 4: Anti-tumor efficacy of the biocompatible suspension of hafnium oxide ($HfO_2$) nanoparticles from example 3 in an NCI-11460-luc2 tumor model xenografted on nude mouse.

Anti-tumor efficacy of the biocompatible suspension of hafnium oxide (HfO$_2$) nanoparticles or nanoparticles aggregates from example 3 in an NCI-H460-luc2 tumor model xenografted in nude mice (see FIG. 4).

After a single injection in tail vein of the biocompatible suspension of hafnium oxide nanoparticles from example 3 (nanoparticles or nanoparticles aggregates concentration equal to 360 g/L and volume of injection equal to 10 ml/kg), three doses of 4 Gy of irradiation (3×4 Gy using a 200 kVp X-ray source) were delivered in the NCI-H460-luc2 tumor (n=5 per group), the first close being delivered 24 h after the administration of the suspension of hafnium oxide. No side effects were observed. No difference in survival of NBTX-IV nanoparticles activated with radiotherapy was observed when compared to the effect obtained with radiotherapy alone, i.e. in the absence of the biocompatible suspension of HfO$_2$ nanoparticles or nanoparticles aggregates from example 3 (control group) (see FIG. 4). The nanoparticles or nanoparticles aggregates have an accumulation factor value equal to 231836 corresponding to a concentration of 2.4 mg of nanoparticles or nanoparticles aggregates per g of tumor (point 3 on FIG. 1).

The invention claimed is:

1. A pharmaceutical composition comprising biocompatible oxide nanoparticles or nanoparticles aggregates wherein i) each of said biocompatible nanoparticle or nanoparticles aggregate is covered with at least one biocompatible alkoxy silane functionalized polyethylene glycol hydrophilic polymer, ii) the longest dimension of each of the biocompatible nanoparticle or nanoparticles aggregate is between about 50 nm and about 150 nm, iii) the surface charge value of each of the biocompatible nanoparticle or nanoparticles aggregate is between −15 mV and +15 mV when measured in an aqueous medium at pH 6-8, and iv) said biocompatible nanoparticles or nanoparticles aggregates have, when administered to a subject in need thereof, an accumulation factor (Accu F) in a targeted tissue of the subject of at least 260500, said Accu F being defined by the equation:

$$\text{Accu } F = \sqrt{(d*Mw)}*C^2,$$

wherein:
- d is the compactness of the at least one biocompatible hydrophilic polymer covering the surface of each of said nanoparticle or nanoparticles aggregate expressed as the number of molecule per nm$^2$ of surface, and d is at least 0.5,
- Mw is the molecular weight of the at least one biocompatible hydrophilic polymer expressed in Kilodalton (kDa), and Mw is between 5 kDa and 20 kDa, and
- C is the concentration of the nanoparticles or nanoparticles aggregates in the pharmaceutical composition expressed in g/L, C being between 350 and 450 g/L, and said Accu F allowing an accumulation of the biocompatible nanoparticles or nanoparticles aggregates of the pharmaceutical composition into the targeted tissue of the subject of at least 4 milligrams (mg) nanoparticles or nanoparticles aggregates per gram (g) of targeted tissue when at least 0.1 g of the pharmaceutical composition per kilogram (kg) of body weight is injected intravenously (IV) or intraarterially (IA) into the subject.

2. The pharmaceutical composition according to claim 1, wherein each of said biocompatible nanoparticle or nanoparticles aggregate is covered with at least two biocompatible hydrophilic polymers and d and Mw are respectively the compactness and the molecular weight of the biocompatible hydrophilic polymer of said at least two biocompatible hydrophilic polymers which exhibits the highest molecular weight.

3. The pharmaceutical composition according to claim 1, wherein the oxide material is HfO$_2$.

4. A method for altering or destroying cells of a targeted tissue in a subject when said cells are exposed to ionizing radiations, wherein the method comprises a step of administering to the subject a pharmaceutical composition comprising biocompatible oxide nanoparticles or nanoparticles aggregates wherein i) each of said biocompatible nanoparticle or nanoparticles aggregate is covered with at least one biocompatible alkoxy silane functionalized polyethylene glycol hydrophilic polymer, ii) the longest dimension of each of the biocompatible nanoparticle or nanoparticles aggregate is between about 50 nm and about 150 nm, iii) the surface charge value of each of the biocompatible nanoparticle or nanoparticles aggregate is between −15 mV and +15 mV when measured in an aqueous medium at pH 6-8, and iv) said biocompatible nanoparticles or nanoparticles aggregates have, when administered to a subject in need thereof, an accumulation factor (Accu F) in a targeted tissue of the subject of at least 260500, said Accu F being defined by the equation:

$$\text{Accu } F = \sqrt{(d*Mw)}*C^2,$$

wherein:
- d is the compactness of the at least one biocompatible hydrophilic polymer covering the surface of each of said nanoparticle or nanoparticles aggregate expressed as the number of molecule per nm$^2$ of surface, and d is at least 0.5,
- Mw is the molecular weight of the at least one biocompatible hydrophilic polymer expressed in Kilodalton (kDa), and Mw is between 5 kDa and 20 kDa, and
- C is the concentration of the nanoparticles or nanoparticles aggregates in the pharmaceutical composition expressed in g/L, C being between 350 and 450 g/L, and said Accu F allowing an accumulation of the biocompatible nanoparticles or nanoparticles aggregates of the pharmaceutical composition into the targeted tissue of the subject of at least 4 milligrams (mg) nanoparticles or nanoparticles aggregates per gram (g) of targeted tissue when at least 0.1 g of the pharmaceutical composition per kilogram (kg) of body weight is injected intravenously (IV) or intraarterially (IA) into the subject, and a step of exposing cells of the targeted tissue to ionizing radiations.

5. The method according to claim 4, wherein the oxide is HfO$_2$.

6. The pharmaceutical composition of claim 1, wherein the nanoparticles or nanoparticles aggregates have a density of at least 7 g/cm$^3$.

7. The method of claim 4, wherein the nanoparticles or nanoparticles aggregates have a density of at least 7 g/cm$^3$.

* * * * *

UNITED STATES PATENT AND TRADEMARK OFFICE
CERTIFICATE OF CORRECTION

PATENT NO. : 10,265,406 B2
APPLICATION NO. : 15/105046
DATED : April 23, 2019
INVENTOR(S) : Agnès Pottier, Laurent Levy and Matthieu Germain It is certified that error appears in the above-identified patent and that said Letters Patent is hereby corrected as shown below:

In the Specification

Column 10,
Line 28, "close" should read --dose--.
Line 29, "close" should read --dose--.

Column 11,
Line 56, "NCI-11460-luc2" should read --NCI-H460-luc2--.

Column 12,
Line 5, "NCI-11460-luc2" should read --NCI-H460-luc2--.

Column 17,
Line 13, "close" should read --dose--.

Signed and Sealed this
Twelfth Day of November, 2019

Andrei Iancu
*Director of the United States Patent and Trademark Office*